US006198293B1

(12) United States Patent
Woskov et al.

(10) Patent No.: US 6,198,293 B1
(45) Date of Patent: Mar. 6, 2001

(54) METHOD AND APPARATUS FOR THICKNESS MEASUREMENT USING MICROWAVES

(75) Inventors: Paul Woskov, Bedford, MA (US); David A. Lamar, West Richland, WA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/048,595

(22) Filed: Mar. 26, 1998

(51) Int. Cl.$^7$ .................................................. G01R 27/00
(52) U.S. Cl. ........................... 324/637; 324/644; 324/642
(58) Field of Search ................... 324/58.5, 644, 324/84; 364/569; 13/32; 422/68

(56) References Cited

U.S. PATENT DOCUMENTS

| | | | |
|---|---|---|---|
| 3,562,642 | * | 2/1971 | Hochschild .......................... 324/58.5 |
| 3,634,756 | * | 1/1972 | Carlise .................................... 324/84 |
| 3,956,572 | * | 5/1976 | Gray .......................................... 13/32 |
| 4,279,019 | * | 7/1981 | Heyser .................................. 364/569 |
| 4,519,982 | * | 5/1985 | Davis, Jr. et al. ..................... 422/68 |
| 5,905,380 | * | 5/1999 | Weiner et al. ........................ 324/644 |

OTHER PUBLICATIONS

B. Dahlberg and M. Brunner, Monitoring Lining Wear Through Laser Beam Technology, AGA IMS 1600, Iron and Steel Engineer, p. 38, Nov. 1982.
L. Galoisy, G. Calas, and M. Maquet, Alumina Fused Cast Quartz Refractory Aging Monitored by Nickel Crystal Chemistry, J. Mater. Res., vol. 6, p. 2434, 1991.
R. A. Strimple, C. R. Beecham, and J. F. Muhlhauser Brick Thickness and Hot–Face Temperature in EAF Sidewalls, Electric Furnace Conference Proc., vol. 31, p. 214, 1974.
M. Konishi, Nagai, T. Horiuchi, Y. Kawate, T. Uehara, K. Shimomura, and H. Sonoi in The On–Line Monitoring Method of Lining Erosion in Blast Furnace, Proc. of the 44th Ironmaking Conf., Iron and Steel Soc. of AIME, p. 511, 1985.
A. S. Prasad, P. Sinha, M. Qamrul, A. Chatterjee, P. K. Chakravarty, in Some Experience with Radio–Isotopes in the Study of the Wear of Blast Furnace Linings, TISCO(tata Iron and Steel Co.) vol. 26, p. 81, 1979.
L. Staicu and I. Apostol in The Use of the (, n) Reaction for Checking Wear of Refractory Lining of Industrial Furnaces, Nuclear Instruments and Methods, vol. 196, p. 511, 1982.
E. Criado, A. Pastor, R. Sancho, Refractories for the Steel Industry, R. Amavis ed., Elsevier Applied Science, London, p. 118, 1990.

* cited by examiner

Primary Examiner—Safet Metjahic
Assistant Examiner—J Nguyen
(74) Attorney, Agent, or Firm—Sam Pasternack, Esq.; Brenda Jarrell; Choate, Hall & Stewart

(57) ABSTRACT

The method for measuring the thickness of a material which transmits a detectable amount of microwave radiation includes irradiating the material with coherent microwave radiation tuned over a frequency range. Reflected microwave radiation is detected, the reflected radiation having maxima and minima over the frequency range as a result of coherent interference of microwaves reflected from reflecting surfaces of the material. The thickness of the material is determined from the period of the maxima and minima along with knowledge of the index of refraction of the material.

10 Claims, 4 Drawing Sheets

METHOD AND APPARATUS FOR THICKNESS MEASUREMENT USING MICROWAVES

This invention was made with government support under Contract number DE-AC06-76RL01830 awarded by the U.S. Department of Energy. The government has certain rights in the invention.

BACKGROUND OF THE INVENTION

This invention relates to thickness measurement and more particularly to such measurement utilizing coherent microwave radiation.

It is often desirable, or even necessary, to determine the thickness of materials when their surfaces are not readily available or are located in hostile environments. For example, high temperature furnaces are lined with refractory materials whose integrity is critical for continued operation of the furnace. Such high temperature furnaces are used in many industries such as the manufacture of materials such as glass and steel, in the remediation of wastes, and for power production. Thus, the refractory insulation lining in such furnaces is subject to the harsh furnace conditions which can cause it to deteriorate. The lifetime of a furnace, which in most cases represents a multi-million dollar capital investment, is determined by the condition of this refractory lining. In addition, the productivity and scheduling of furnace facility operations is determined in part by requirements for minimizing refractory wear, or refractory inspections, and for refurbishment.

It is important to be able to monitor the condition of the refractory material while the furnace is in operation. Such real-time monitoring capability improves the productivity and lifetime of furnace facilities. Unnecessary furnace downtime for refractory inspections can be minimized and furnace operations which cause rapid refractory deterioration can be quickly corrected before significant damage is done. In addition, with real-time monitoring, timely corrective action can be taken once the refractory deterioration has reached a critical stage so as to prevent a catastrophic furnace failure. It is also desirable to monitor refractory condition without needing access to the interior of the furnace because of its hostile environment.

A number of methods and instruments have been developed heretofore and used for refractory lining thickness measurements. All of the known existing methods and devices require either access into the furnace to view internal exposed surfaces or special modifications in the furnace lining itself such as, for example, to embed instruments or to add special materials such as radioactive tracers during furnace lining construction. Other techniques involve indirect methods which rely on mathematical temperature models. No known prior art technique functions by simply viewing the outside of the refractory lining.

Instruments and techniques that require internal furnace access such as laser beam interferometry technology (See, B. Dahlberg and M. Brunner, *Monitoring Lining Wear Through Laser Beam Technology*, AGA IMS 1600, Iron and Steel Engineer, p.38, Nov. 1982) and a proposed diffuse reflectance spectroscopy method (L. Galoisy, G. Calas, and M. Maquet, *Alumina Fused Cast Quartz Refractory Aging Monitored by Nickel Crystal Chemistry*, J. Mater. Res., Vol. 6, p. 2434, 1991) are limited to furnaces that have visible access to view internal refractory lining surfaces. Such visible access is not possible in many furnaces to all the surfaces that need to be monitored and particularly so when they are in operation. In addition, optical viewing techniques are not robust in furnace environments which can have smoky and otherwise dirty atmospheres that can obscure views. Laser interferometry techniques are also very sensitive to vibrations and such sensitivity complicates use of this instrumentation in an industrial environment. Further, the reflectance spectroscopy method referred to above does not measure refractory thickness but only chemical changes in the surface of the refractory material.

Embedding wire loops and thermocouples into the refractory lining has also been used to determine refractory thickness. R. A. Strimple, C. R. Beechan, and J. F. Muhlhauser in *Monitoring Brick Thickness and Hot-Face Temperature in EAF Sidewalls*, Electric Furnace Conference Proc., Vol. 31, p. 214, 1974, describe a method utilizing wire loops spaced at 1 inch distances along the depth of the refractory and monitoring the loss of loop conductivity as the furnace lining wears through to break the loops. This method is limited in its spatial resolution of the lining thickness and in the number of points that can be monitored. The embedded wire loops may also be points of weakness at which the refractory lining might fail. M. Konishi, N. Nagai, T. Horiuchi, Y. Kawate, T. Uehara, K. Shimomura, and H. Sonoi in *The On-Line Monitoring Method of Lining Erosion in Blast Furnace*, Proc, of the 44th Ironmaking Conf., Iron and Steel Soc. of AIME, p. 511, 1985, have used methods that employ multiple thermocouples in the refractory lining from which thermal models are used to calculate refractory thicknesses. One thermal model relies on the time response of thermal fluctuations propagating through the refractory and another on the calculation of isothermals in the refractory. This approach is an indirect thickness measurement technique which can only be as accurate as the assumptions relied upon in the models.

Nuclear techniques have also been used and/or proposed for monitoring furnace lining wear. A. S. Prasad, P. Sinha, M. Qamrul, A. Chatterjee, P. K. Chakravarty, in *Some Experience with Radio-Isotopes in the Study of the Wear of Blast Furnace Linings*, TISCO(Tata Iron and Steel Co.) Vol. 26, p. 81, 1979, have used radioactive isotopes installed in the furnace lining and monitored the gamma radiation to study lining wear. Radioactively contaminating a furnace so as to monitor refractory corrosion is obviously of limited applicability. L. Staicu and I. Apostol in *The Use of the ($\lambda$, n) Reaction for Checking Wear of Refractory Lining of Industrial Furnaces*, Nuclear Instruments and Methods, Vol. 196, p. 511, 1982, have proposed a gamma-neutron reaction monitor in which the gamma source is safely contained but causes the emission of neutrons from a beryllium oxide sample attached to the exposed surface of the refractory. As the beryllium sample wears away, the neutron signal decreases. This method eliminates radioactive contamination of the furnace, but beryllium itself is a highly toxic metal which could not be readily used in many furnace installations.

SUMMARY OF THE INVENTION

In one aspect, the method for measuring the thickness of a material which transmits a detectable amount of microwave radiation includes irradiating the material with coherent microwave radiation tuned over a frequency range. Reflected microwave radiation from the material is detected. This reflected radiation has maxima and minima over the frequency range as a result of coherent interference of microwaves reflected from reflecting surfaces of the material. The thickness of the material is determined from the period of the maxima and the minima and from the index of refraction of the material. In a preferred embodiment the material whose thickness is to be determined is a refractory material which may form the lining within a high temperature furnace, examples of such refractory materials include, but are not limited to, alumina-silica magnesite, magnesite-chrome, magnesite-spinel, zircon, alumina-zirconia-silica (AZS), stabilized zirconia, dolime, magnesite-dolime, fireclay, firebrick, fused AZS, and fused chrome spinel. In another embodiment, the Fourier transform of the reflected radiation signal is taken which will provide a peak in the power spectrum for each layer of insulating material.

The method of the invention is generally applicable to the measurement of thickness of materials which transmit detectable amounts of microwave radiation. For example, the method of the invention can be used to measure the thickness of ice on the surface of a body of water.

The microwave refractory corrosion monitor of the invention does not require internal furnace access, is robust in the furnace facility environment, does not require modifications to the furnace refractory lining, does not rely on thermal models, is a direct real-time measurement of thickness, and does not contaminate the furnace. The methodology thus overcomes the limitations of all known devices and proposed methods for monitoring refractory deterioration.

The technology disclosed and claimed herein is applicable in a number of large industries which use high temperature furnaces. The iron and steel making industry is the largest consumer of refractory lining materials accounting for 60–65% of the market in developed countries. See E. Criado, A. Pastor, R. Sancho, *Refractories for the Steel Industry*, R. Amavis ed., Elsevier Applied Science, London, p. 118, 1990. The microwave refractory corrosion monitor of the invention represents a new technology which can reduce refractory consumption costs and improve steel productivity. The glass industry is another application for the present technology. Other applications include non-ferrous pyrometallurgical industries for the production of copper, nickel and other metals. Furnaces in the high temperature waste processing industry are another application. Yet another application is in power production plants using high temperature furnaces.

DESCRIPTION OF THE PREFERRED EMBODIMENT

Figure 1:
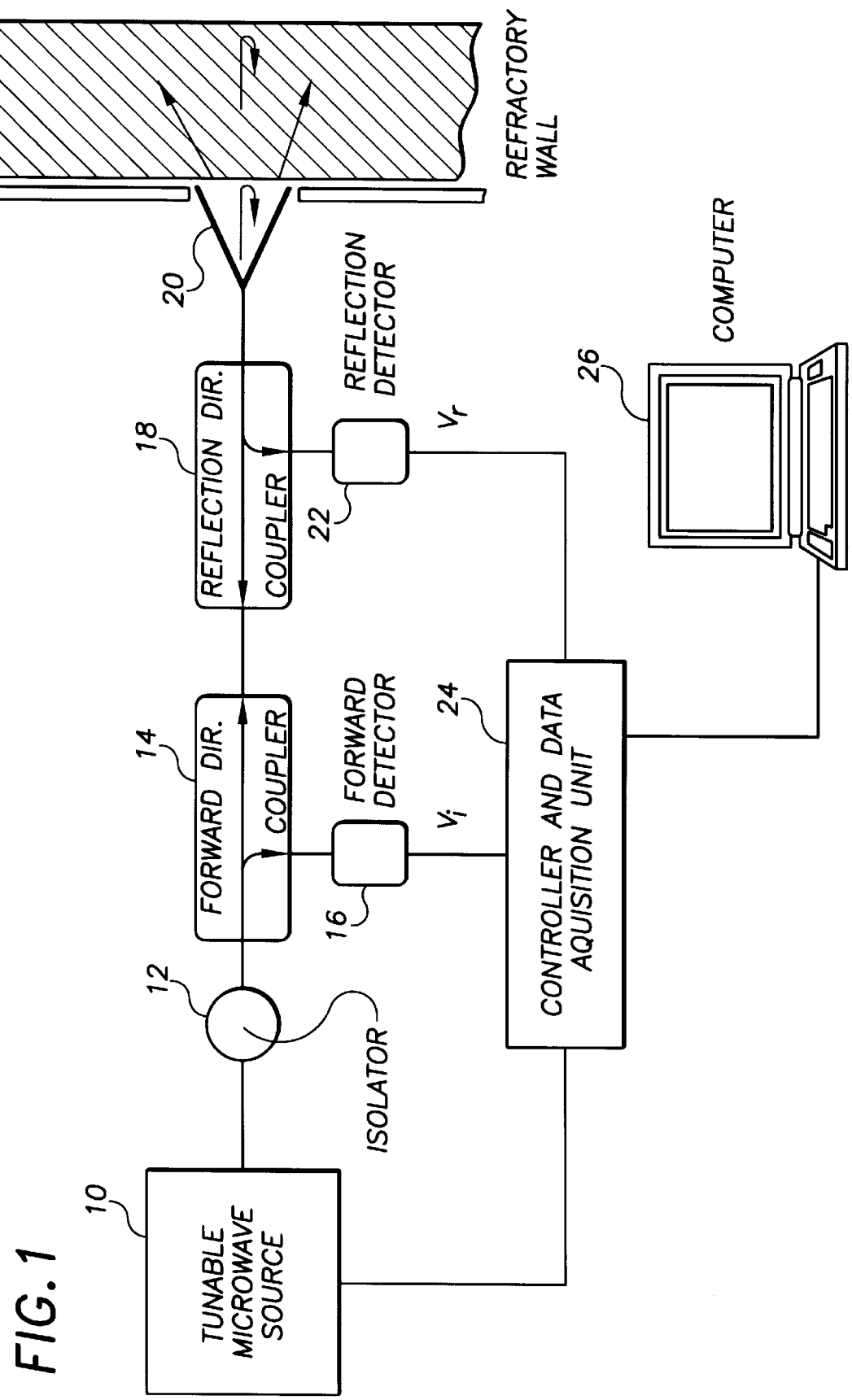
FIG. 1 is a schematic illustration of the microwave refractory monitor apparatus of the invention.

First of all, the theory on which this invention is based will be described. The monitoring device of the invention uses coherent microwave radiation that propagates into a refractory furnace lining from outside the furnace and is partially reflected by each refractory surface. Tuning the microwave frequency over a selected range causes the total reflected signal level, which is the coherent summation of the reflections from each refractory surface, to vary between maxima and minima. The period of the maxima and minima as a function of tuned frequency is linearly proportional to the refractory thickness for a given refractory index of refraction. The relationship between the refractory thickness and the frequency between successive peaks in the reflected signal is given by:

$$h = \frac{c}{2fn} \quad (1)$$

where h is the refractory thickness, c is the speed of light, f is the frequency separation between successive peaks or minima in the total reflected signal, and n is the index of refraction of the refractory material.

For those familiar with optics, the above equation 1 is precisely the same relationship for the longitudinal mode frequency separation in a Fabry-Perot resonator. See, Born and Wolf, *Principles of Optics*, Pergamon Press, New York, 4th ed., 1964. A Fabry-Perot resonator is formed by two parallel reflectors either flat or curved, in this case the surfaces of the refractory. Fabry-Perot resonators with high reflectivity mirror surfaces are in wide use as laser cavities and etalon interference filters; consequently Equation 1 in a slightly different form is very well known.

At microwave frequencies rough refractory surfaces appear smooth, setting up well defined "resonances" (maxima or minima in the reflected signal as a function of frequency). For example, surface roughness on the order of one inch such as cracks and/or spallation pits in the refractory surfaces would not significantly attenuate the resonances at frequencies below 10 GHz. Since frequency can be measured with very high precision and the index of refraction of refractory materials can be well characterized by laboratory measurements, mean refractory thickness measurements with a resolution that is a very small fraction of one inch is possible.

The refractory thickness measurement method of the invention is also effective when there are multiple layers of different refractory materials in the furnace lining. In this case the total reflected signal is a superposition of more than one period as a function of frequency. Each pair of abrupt changes in the index of refraction along the direction of a microwave beam propagation will have its own unique reflection period. A Fourier transform of the reflected signal record as a function of frequency will identify the resonances associated with each layer of refractory material in the furnace lining. See, R. N. Bracewell, *The Fourier Transform and its Application*, McGraw-Hill, New York, 2nd ed., 1978. The simultaneous measurement of the deterioration of the refractory layer that is exposed inside the furnace along with swelling of intermediate layers is possible.

A preferred instrument embodiment in illustrated in FIG. 1. The microwave power used for the refractory furnace wall thickness measurements originates in a frequency tunable microwave source 10 such as a YIG tuned Gunn oscillator. A YIG tuned Gunn oscillator is a rugged solid-state source of coherent microwave power having a broad range of frequency tunability (for example 7–12.4 GHz). Nominal power output of 0.1 watt is sufficient for producing detectable signals in many refractory materials. An isolator 12 protects the microwave source 10 from reflections which could affect this source's performance. Microwave power travels through a forward directional coupler 14 which directs a small fraction, −10 dB or less, of the forward transmitted power to a detector 16 which produces a signal $V_f$, proportional to the forward power. Next, the microwave power passes through a reflection directional coupler 18 and is launched by a microwave antenna 20 such as a horn antenna into the refractory wall. If the furnace or melter is contained by a metal shell, a hole in the metal shell provides access to the refractory wall. A part of the launched microwave beam is reflected by each refractory surface and travels back into the microwave antenna. A fraction of this reflected signal, −3 dB or less, is directed by the reflection directional coupler 18 to a detector 22 which produces a signal $V_r$, proportional to the total reflected power. The detectors, 16 and 22, can be solid-state diode detectors such as the Schottky diode type with sensitivities of better than $10^{-6}$ watt signal levels, or more sophisticated detection circuits with sensitivities to significantly smaller signal levels.

A controller and data acquisition unit 24 provides a signal to tune the microwave source through a selected frequency range such as, for example, 7–12 GHz and to simultaneously acquire and digitize the forward and reflected signals $V_i$ and $V_r$. This unit 24 is controlled by a computer 26 which commands the microwave tuning and stores the data, displays it, and processes it to determine refractory layer thickness using Equation 1. The computer software may be programmed to provide an alarm or automatic feedback to furnace control if the furnace lining reaches a predetermined state of deterioration.

Figure 2:
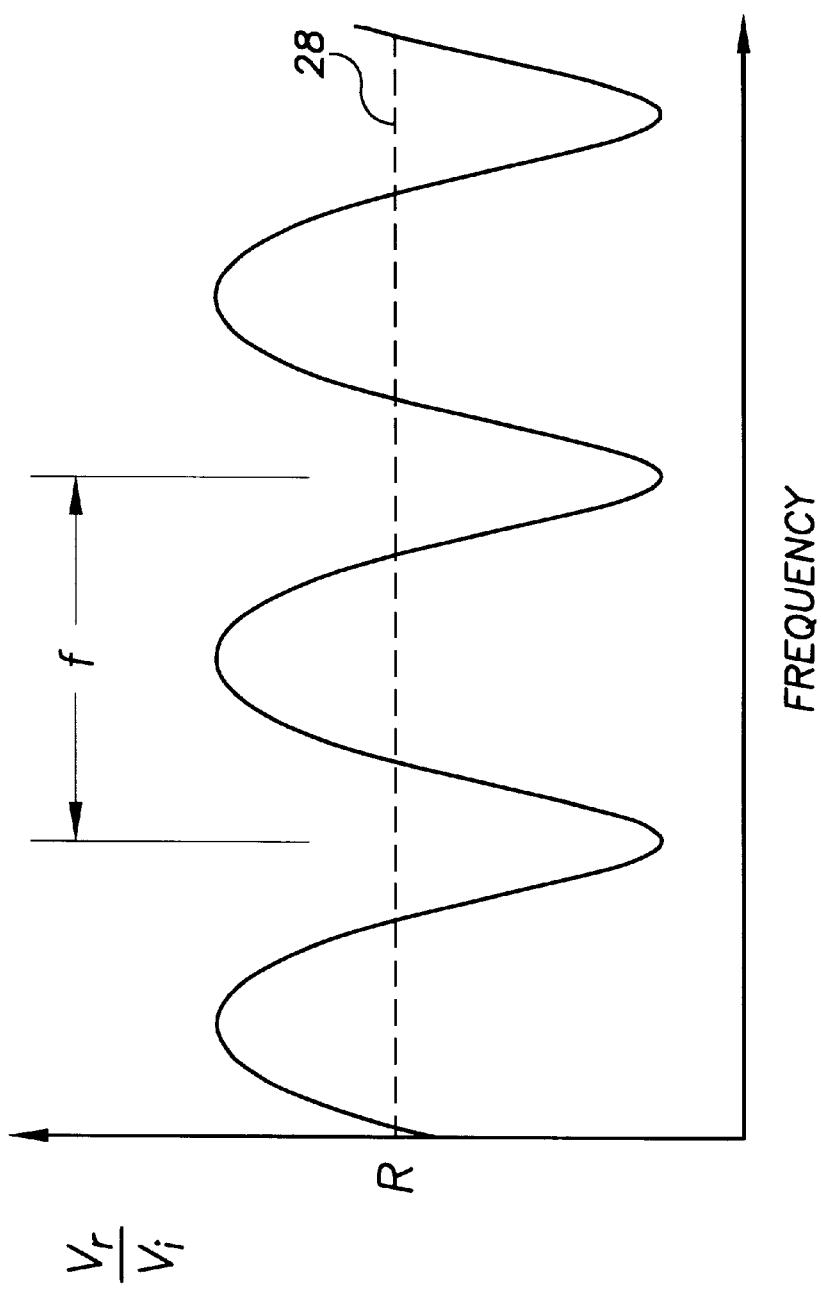
FIG. 2 is a graph of the ratio of reflected power to incident power as a function of frequency.

FIG. 2 illustrates data for a refractory lining of a single material having only two surfaces which reflect the microwave beam. The ratio of $V_r$ to $V_i$ is plotted as a function of tuned microwave frequency. The period of the maxima and minima as indicated by f in FIG. 2 is used in Equation 1 to determine the refractory thickness. Measuring the period between minima is preferable because they are sharper than the maxima. In the case of more than two refractory surfaces (multiple layers of different materials) the $V_r$ to $V_i$ ratio as a function of frequency is a superposition of more than one period and a Fourier transform is performed by the computer 26 to determine the f parameter for the various refractory layers as will be discussed below in conjunction with FIGS. 3 and 4.

Additional information can be obtained from the data record as illustrated in FIG. 2. If the reflected signal is absolutely calibrated, the mean level of reflected signal strength as illustrated by R and the dashed line 28 can be used to determine the index of refraction of the reflecting refractory material. As is well known in optics, the relationship between the index of refraction and the surface reflectivity of the intensity of electromagnetic radiation at normal incidence on a dielectric surface is given by:

$$n = \frac{1 + \sqrt{R}}{1 - \sqrt{R}} \quad (2)$$

The index of refraction determined in this way would correspond to that at the first surface nearest the antenna 20.

It is therefore possible, in principle, that the refractory corrosion monitor as shown in FIG. 1 could make refractory thickness measurements without any prior knowledge of the refractory index of refraction. However, this would only be strictly true if there are no significant gradients in the index of refraction inside the layer being monitored. Such gradients could be present if the index of refraction varies with temperature and there are thermal gradients in the layer being monitored.

The microwave refractory corrosion monitor of the invention was tested in the laboratory with a GP Green AD-99 alumina brick and a Harbison-Walker chromium-alumina brick at temperatures up to 2200° F. The tests were carried out in a small laboratory furnace at the Plasma Science and Fusion Center at the Massachusetts Institute of Technology.

Figure 3:
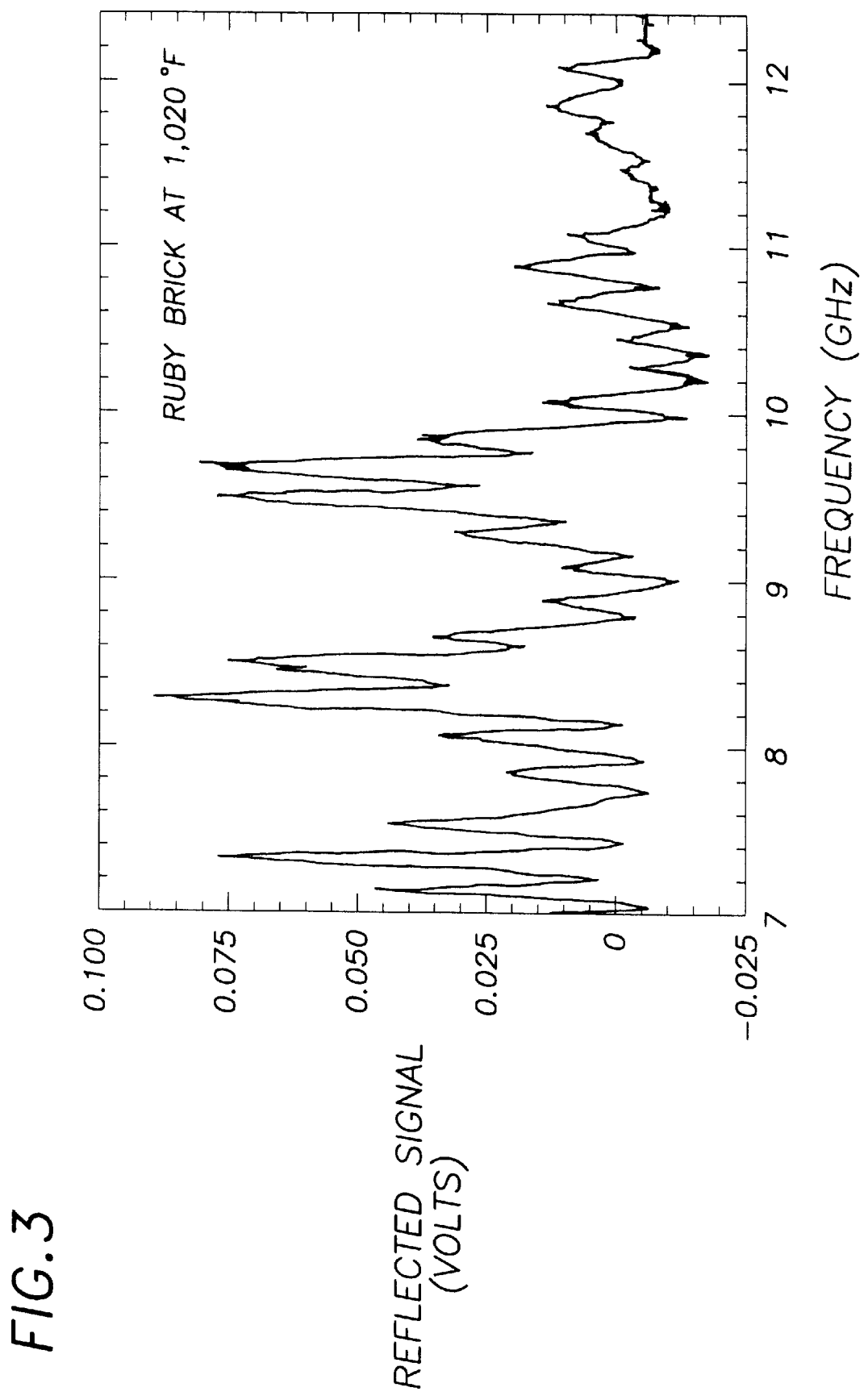
FIG. 3 is a graph of reflected signal vs. frequency for a particular experiment.

In addition to testing the feasibility of this monitor at high temperatures, the goal of these measurements was also to catalog the high temperature microwave refractive indices of these refractory materials and to see if they vary with temperature. FIG. 3 illustrates the type of data that was obtained with the Harrison-Walker high-alumina RUBY-SR brick. For the measurement shown in this figure the brick was completely soaked inside the furnace at a temperature of 1,020° F. The 9 inch long brick was stood vertically on end on approximately 4.3 inches of fiber board insulation which formed the bottom of the furnace enclosure. The microwave horn viewed this brick from the bottom upward through the fiber board insulation.

Figure 4:
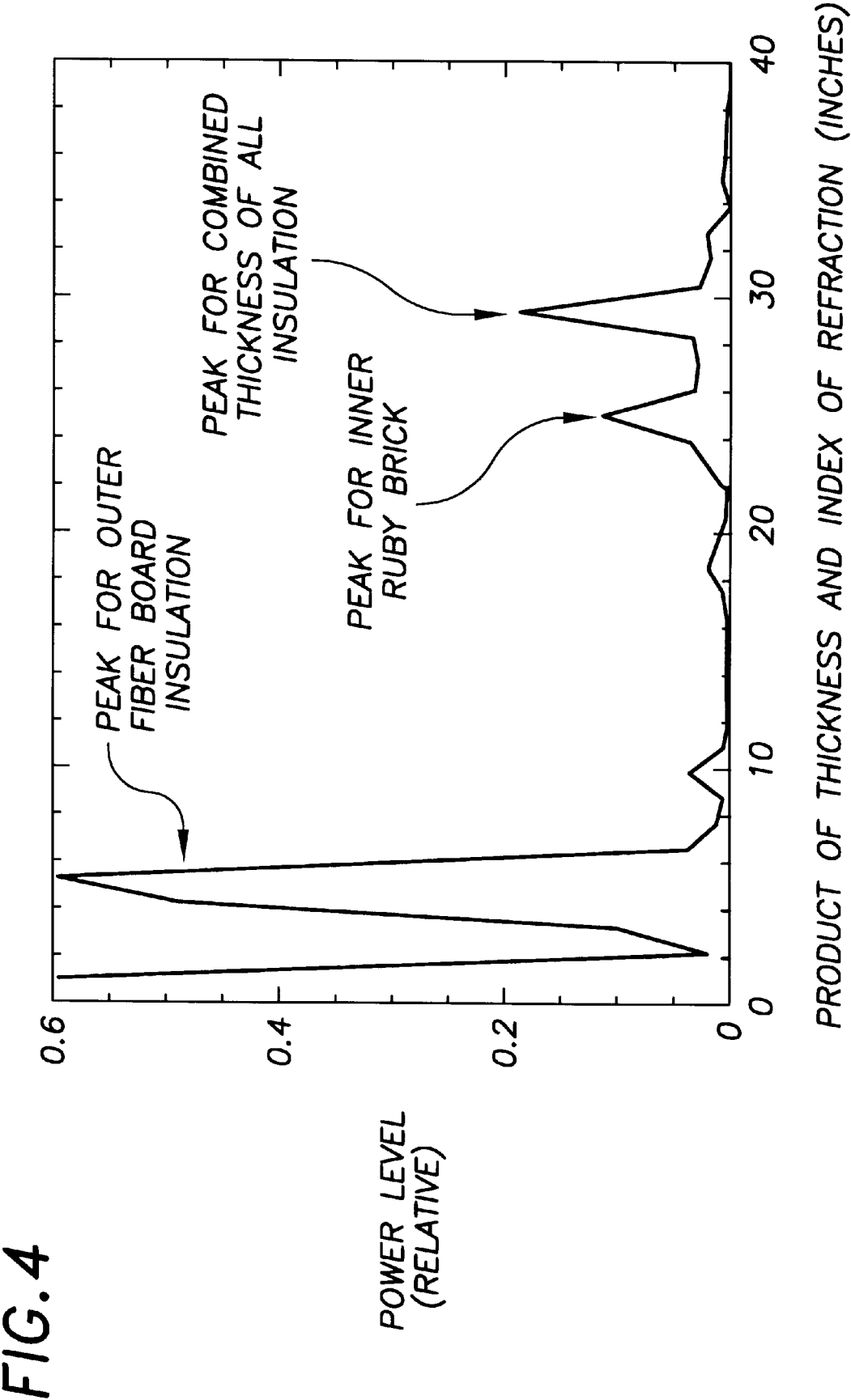
FIG. 4 is a graph of the Fourier transform power spectrum of the signal in FIG. 3 showing the thickness.

The graph in FIG. 3 shows the reflected microwave signal as the microwave frequency was tuned. The signal is modulated by several periods of interference peaks and minima corresponding to the various pairings of reflecting surfaces along the microwave direction of view. The graph in FIG. 4 shows the Fourier transformed power spectrum of the reflection signal of FIG. 3. There is a peak in the power spectrum for each layer of insulating material, as well as a peak for the total insulation thickness comprising all layers. The location of the spectrum peaks along an x-axis is linearly proportional to the product of the layer thickness and index of refraction. The index of refraction is easily tabulated from this data and can be used for future measurements of these materials in actual process furnace installations. We have found, up to the maximum temperatures so far tested (2200° F.), that the refractive index is a constant. Therefore, refractory corrosion would simply be displayed as a shifting of the peak to the left in the power spectrum. A change of only 1 mm in the refractory thickness may be readily observed.

If a furnace lining is constructed of refractory material that has some transparency to microwaves such as fiber board, alumina, and chrom-alumina, then FIGS. 3 and 4 demonstrate the capability of the microwave refractory corrosion monitor of the invention to measure the thickness of all layers of insulation in a furnace simultaneously. Wear of an inner layer along with possible swelling of outer layers can be clearly monitored with only a view of the outer surface of the furnace lining. The measurement can be accomplished without any access into the furnace while the refractory is hot. No other demonstrated refractory monitoring technology has this capability.

The monitoring technique disclosed herein is sensitive to a variety of possible refractory failure modes. Refractory can corrode or wear thin, it can soak up slag, or it can change chemically in other ways. Each of these failure modes has a boundary in the refractory material which would cause reflection of the microwave beam and thus be detectable. Build up of a slag crust on the surface of the refractory would also be observable. In addition, because the phase of an electromagnetic reflection from an electrically conducting surface is different from that of a nonconducting surface, the level of the molten slag inside the furnace could be inferred from a number of refractory thickness measurements at different locations.

The main requirements for this monitoring technique are: a view of the outside of the furnace refractory lining (access through any outside metal shell), refractory materials through which detectable levels of microwaves can propagate, knowledge of the index of refraction of the refractory material or materials, and knowledge of furnace temperature if the index of refraction is a function of temperature. This technique can be simply implemented and can be highly accurate. It is not to be confused with radar techniques which measure distances by time of flight, requiring much more sophisticated electronics. This is a novel new application of microwave technology which is optimum for dielectric layer thickness measurements and is completely different from radar instrumentation.

While the present invention has been described in conjunction with the measurement of the thickness of refractory materials in furnaces, the disclosed techniques have broader applicability. The method may be used to measure the thickness of any material which transmits a detectable amount of microwave radiation. One example is the measurement of the thickness of ice coatings on bodies of water or on metal surfaces.

It is intended that all variations and modifications of the invention disclosed herein be included within the scope of the appended claims.

What is claimed is:

1. Method for measuring the thickness of a material which transmits a detectable amount of microwave radiation comprising:

irradiating the material with coherent microwave radiation tuned over a frequency range;

simultaneously detecting reflected microwave radiation from the material as the microwave radiation is tuned over said frequency range, the reflected radiation having maxima and minima over the frequency range as a result of coherent interference of microwaves reflected from reflecting surfaces of the material; and determining the thickness of the material from the period of the maxima and minima and from the index of refraction of the material.

2. The method of claim 1 wherein the material is a refractory material.

3. The method of claim 1 further including taking the Fourier transform of the reflected radiation signal.

4. The method of claim 2 wherein the refractory material is a furnace lining.

5. Method for measuring the thickness of a refractory material in a furnace comprising:

irradiating the refractory material with coherent microwave radiation tuned over a frequency range;

simultaneously detecting reflected microwave radiation from the material as the microwave radiation is tuned over said frequency range, the reflected radiation having maxima and minima over the frequency range as a result of coherent interference of microwaves reflected from reflecting surfaces of the material; and determining the thickness of the material from the period of the maxima and minima and from the index of refraction of the refractory material.

6. The method of claim 5 wherein the frequency range is approximately 7–12 GHz.

7. The method of claim 5 wherein the refractory material is alumina brick.

8. The method of claim 5 wherein the refractory material is chromium-alumina brick.

9. The method of claim 5 wherein the refractory material is silica brick.

10. Apparatus for measuring the thickness of a material which transmits a detectable amount of microwave radiation comprising:

a source of coherent microwave radiation tuned over a frequency range and directed toward the material;

a detector for simultaneously receiving microwave radiation reflected from the material as the microwave radiation is tuned over said frequency range, the reflected radiation having maxima and minima over the frequency range as a result of coherent interference of microwaves reflected from reflecting surfaces of the material; and means for determining thickness of the material from the period of the maxima and minima and from the index of refraction of the material.

* * * * *